US012721578B2

(12) United States Patent
Hoffmann et al.

(10) Patent No.: US 12,721,578 B2
(45) Date of Patent: Sep. 1, 2026

(54) METHOD AND APPARATUS FOR DETERMINING AN X-RAY IMAGE DATASET

(71) Applicant: Otto-von-Guericke-Universitaet Magdeburg, Magdeburg (DE)

(72) Inventors: Thomas Hoffmann, Magdeburg (DE); Tim Pfeiffer, Magdeburg (DE); Robert Frysch, Welsleben (DE); André Mewes, Magdeburg (DE); Benjamin Fritsch, Magdeburg (DE); Georg Rose, Magdeburg (DE)

(73) Assignee: OTTO-VON-GUERICKE-UNIVERSITAET MAGDEBURG, Magdeburg (DE)

( * ) Notice: Subject to any disclaimer, the term of this patent is extended or adjusted under 35 U.S.C. 154(b) by 143 days.

(21) Appl. No.: 18/720,626

(22) PCT Filed: Nov. 10, 2022

(86) PCT No.: PCT/EP2022/081524
§ 371 (c)(1),
(2) Date: Jun. 15, 2024

(87) PCT Pub. No.: WO2023/110239
PCT Pub. Date: Jun. 22, 2023

(65) Prior Publication Data

US 2025/0049401 A1 Feb. 13, 2025

(30) Foreign Application Priority Data

Dec. 16, 2021 (DE) ........................ 102021133450.0

(51) Int. Cl.
*A61B 6/00* (2024.01)
*A61B 6/06* (2006.01)

(52) U.S. Cl.
CPC .................................... *A61B 6/06* (2013.01)

(58) Field of Classification Search
CPC ..................................................... A61B 6/032
See application file for complete search history.

(56) References Cited

U.S. PATENT DOCUMENTS

2008/0002806 A1* 1/2008 Nishide ................. G06T 11/005
378/4

FOREIGN PATENT DOCUMENTS

| CA | 2733415 A1 | 9/2012 |
|---|---|---|
| DE | 102016219817 B4 | 5/2018 |

OTHER PUBLICATIONS

Schafer et al., "Filtered region of interest cone-beam rotational angiography," Med. Phys., 37(2):694-703 (2010).

(Continued)

*Primary Examiner* — Dani Fox
(74) *Attorney, Agent, or Firm* — KRIEGSMAN & KRIEGSMAN

(57) ABSTRACT

Method for determining an X-ray image dataset of a target region of an object to be examined, wherein projection images showing the target region are captured by an X-ray detector and the X-ray image dataset is reconstructed from the projection images, wherein a first portion of the projection images is captured so as to be collimated onto the target region by the target region being irradiated with X-ray radiation by an X-ray device through at least one main radiation opening of a collimator assembly. The invention also relates to a corresponding apparatus for determining an X-ray image dataset of a target region of the object to be examined. The invention generally relates to the field of medical X-ray imaging, in particular with the aim of acquiring projections for reconstructing 2D computed-tomography images.

11 Claims, 3 Drawing Sheets

(56) References Cited

OTHER PUBLICATIONS

Figure 2:
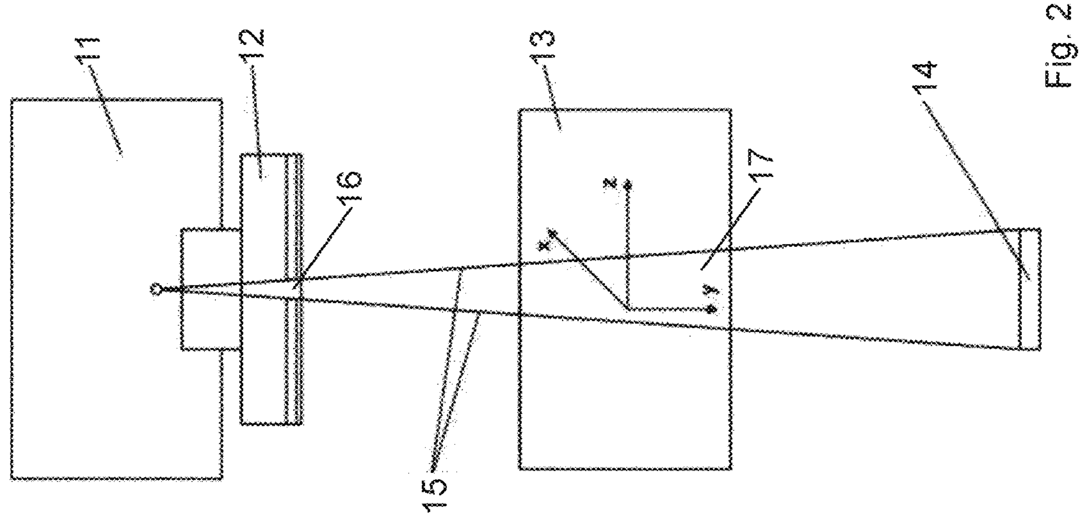

Hashimoto et al., "Dose reduction technique in diagnostic X-ray computed tomography by use of 6-channel multileaf collimators," Radiological Physics and Technology, 10(1):60-67 (2017).

* cited by examiner

METHOD AND APPARATUS FOR DETERMINING AN X-RAY IMAGE DATASET

The invention relates to a method for determining an X-ray image data set of a target area of an examination object, wherein projection images showing the target area are taken by means of an X-ray detector and the X-ray image data set is reconstructed from the projection images, wherein a first part of the projection images are taken collimated onto the target area by the target area being irradiated with X-ray radiation by means of an X-ray device through at least one main radiation opening of a collimator assembly. The invention furthermore relates to a respective apparatus for determining an X-ray image data set of a target area of the examination object. In general, the invention relates to the field of medical X-ray imaging, in particular with the aim of acquiring projections for reconstructing computed tomography sectional images.

One aspect of the invention includes a collimator for restricting an X-ray beam for computed tomography imaging. A collimator constitutes a mechanical or mechatronic device that restricts the beam path between an X-ray device (X-ray tube) and X-ray detector to a defined area for example by means of motorized or manual positioning of lamellae made of a strongly X-ray-debilitating material. The lamellae can be straight or curved, can have different thicknesses, and can contain chamfers, for example, to ensure a more precise transillumination. The aim is to transilluminate the patient with a preferably low radiation dose that is sufficient for imaging. A collimator is used, for example, in radiography systems (planar transillumination) and angiography systems (also planar transillumination) and computed tomography systems. In various constructions, with the aim of local irradiation of the patient, so-called multi-lamella collimators are also used for radiotherapy.

In this type of the first mentioned construction with the aim of imaging, the collimator is installed directly in front of the X-ray tube to specifically adjust the beam path between X-ray tube and X-ray detector. Between collimator and X-ray detector, the examination object (e.g., patient, phantom, animal, construction part, etc.) is usually positioned on a table.

The invention described here relates, for example, to collimators for generating projection images as basis for 3D sectional image calculation (so-called reconstruction). In this type of imaging, the beam path is in general adjusted along the z-axis (longitudinal axis of the patient). This has the reason that in detector systems with more than one row also individual rows can be irradiated. In many cases, the irradiation of all rows is not necessary to be able to examine the targeted body area in the reconstructed sectional image.

A further application of the invention is the so-called flat detector computed tomography. This is often carried out using so-called C-arm X-ray systems. In this field, the method of volume of interest (VOI) sectional image generation has become established. Here, the patient is only partially transilluminated in an area of interest (target area). As a rule, today still a complete transillumination of the entire examination object (patient) takes place to avoid so-called truncation artefacts in the reconstructed image. Truncation artefacts occur when the examination object cannot be completely captured. This results in a loss of information of the non-captured areas, which leads to a further loss of required information during image calculation.

Volume of interest CT thus offers the advantage of dose reduction for the examination object, but at the same time usually causes the disadvantage of artefact-ridden (incomplete) images.

In today's CT diagnostics, complete CT images are preferably acquired for this reason, as a preferably high image quality must be achieved. The reason for this is that in the context of diagnostics it is often unclear in advance what the patient is suffering from and in which area of the body the pathology or pathologies are located.

VOI imaging is used-particularly in flat detector CT-when the area to be examined is already known in advance (e.g., for therapy control after implantation of a stent in the arteries of the brain). With the current state of the art, however, those VOI CT images are heavily artefact-ridden, especially in the marginal areas and do not represent the real Hounsfield values of the examination object, but are afflicted with an unknown offset value.

In order to still be able to use the advantage of dose reduction, various methods for compensating the "lost" image information have already been published. For example, mathematical transition models from the marginal areas to the object are used, which make assumptions about the geometry and attenuation properties in the non-transilluminated areas. Further methods use specific advance information from previously created data sets (e.g., CT, MRI, ultrasound, surface scans or other methods).

From DE 10 2016 219 817 B4 proposals are derived for reducing truncation artefacts in X-ray image data sets.

The problem of the invention is to provide a method and an apparatus for determining an X-ray image data set, in which a high image quality of a limited target area of an examination object can be achieved with a preferably low X-ray dose.

This problem is solved with a method as mentioned at the beginning by taking a second part of the projection images to reduce truncation artefacts in the X-ray image data set by irradiating marginal regions of the target area with X-ray radiation with one or several secondary radiation openings of the collimator assembly, which surround the main radiation opening or are adjacent to it, and determining the X-ray image data set from the first part of the projection images with the aid of the second part of the projection images. In this way, the target area, also known as the volume of interest, can be determined adaptively with sufficient image quality and the X-ray dose can be minimized at the same time.

According to the invention, the secondary radiation opening(s) of the collimator assembly have a certain transmittance for the X-ray radiation. Through the secondary radiation openings, further spatially limited areas of the examination object are irradiated with X-ray radiation. A secondary radiation opening does not necessarily have to be completely "open" in the sense of through-opening, but can be completely or partially closed with a material or a combination of materials, as long as there is sufficient radiolucency for the X-ray radiation. A secondary radiation opening can, for example, be designed as a complete material recess in a collimator aperture, or by thinning the material through which a sufficient amount of X-ray radiation can pass through. It is also conceivable to design such a secondary radiation opening by means of an insert made of a material that has a lower absorption of X-rays than the surrounding material of the collimator aperture, so that a high mechanical load-bearing capacity of the collimator aperture can still be ensured.

The method may include one or both of the following features:

- projection images showing the target area can be taken from different projection directions along an acquisition trajectory,
- a higher dimensional X-ray image data set can be reconstructed from the projection images, i.e., with more dimensions than the projection images.

According to an advantageous embodiment of the invention, it is provided that the size, position and/or radiolucency of one, several or all secondary radiation openings are varied during an X-ray examination of the target area. This allows an improved adaptation of the functionality of the secondary radiation openings during an X-ray examination, so that, if applicable depending on the image quality achieved in the X-ray images, an adjustment of the size, position and/or radiolucency can be made. For example, the collimator assembly can have adjustable collimator apertures by which one or more of the parameters size, position and/or radiolucency in secondary radiation openings can be changed. This can also further reduce the radiation exposure of the examination object.

According to an advantageous embodiment of the invention, it is provided that the variation of the size, position and/or radiolucency of one, several or all secondary radiation openings is carried out adaptively in dependence of the respective quality of the present X-ray images. This allows in a particularly advantageous way an adaptive adjustment of the marginal areas of the collimator assembly irradiated by the secondary radiation openings during image acquisition. The background to this is that, if the image quality of the X-ray images falls below or exceeds a certain level, e.g., determined by the characteristics of truncation artefacts or a specific signal-to-noise ratio, the secondary radiation openings can be adaptively adjusted with regard to the mentioned parameters, e.g., can be opened further or closed further, up to a completely closed state, to ensure the lowest radiation dose with sufficient image quality at all times.

According to an advantageous embodiment of the invention it is provided that the method has an automatic detection of irradiated and non-irradiated regions of the X-ray detector and an automatic consideration of detected irradiated and non-irradiated regions of the X-ray detector in the determination of the X-ray image data set. In this way, the method according to the invention is also suitable for carrying out iterative image reconstruction methods. In such an image reconstruction method, information of individual image pixels can be taken into account or neglected in the process of image calculation. For this purpose, it is necessary to automatically detect exposed (irradiated) and unexposed (non-irradiated) regions of the X-ray detector. The detection of irradiated and non-irradiated regions or exposed and non-exposed regions of the X-ray detector can be carried out, for example, by calculation based on the position of apertures of the collimator assembly, e.g., depending on the setting of the parameters of the secondary radiation openings, possibly taking into account the geometric conditions between the X-ray device, the collimator assembly and the X-ray detector. A real-time evaluation of the image pixel information of the X-ray detector itself can also be carried out, e.g., by means of a threshold value method.

According to an advantageous embodiment of the invention, it is provided that the method has one automatic detection of scattered radiation of the emitted X-ray radiation in regions of the X-ray detector, which are not directly irradiated, and an automatic consideration of detected scattered radiation in the determination of the X-ray image data set. In this way, the image quality of the X-ray images can be further improved and/or the radiation dose required for their acquisition can be further lowered. For example, the incoming X-ray radiation in the non-directly exposed regions of the X-ray detector, which nevertheless occur there due to scattering effects (scattered radiation), can be measured and included in the determination of the X-ray imaged data set, taking physical models of the system into account. Regions of the X-ray detector that are not directly irradiated are, for example, the areas between which there is no linear connection between the X-ray device and the X-ray detector through at least one main radiation opening or at least one secondary radiation opening.

The said problem mentioned above is also solved by an apparatus for determining an X-ray image data set of a target area of an examination object, having an X-ray detector for taking projection images showing the target area and a reconstruction means for reconstructing the X-ray image data set from the projection images, further having an X-ray device and a collimator assembly having at least one main radiation opening for taking a first part of the projection images, which are taken collimated onto the target area by the target area being irradiated with X-ray radiation by means of an X-ray device, wherein the collimator assembly has one or several secondary radiation openings, which surround the main radiation opening or are adjacent to it, wherein a second part of the projection images is taken by irradiating marginal regions of the target area with X-ray radiation through the one or the several secondary radiation openings, wherein the reconstruction means is arranged to determine the X-ray image data set from the first part of the projection images with the aid of the second part of the projection images to reduce truncation artefacts in the X-ray image data set. This also realizes the advantages as described before.

According to one advantageous embodiment of the invention it is provided that the collimator assembly is arranged to adjust the width and/or the length of one, several or all secondary radiation openings. For example, the apparatus can have an automatic drive, e.g., via motors, for the adjustment of the width and/or length of the secondary openings. In this way, certain parameters of the secondary opening can be varied, in particular size, position and/or radiolucency.

According to an advantageous embodiment of the invention it is provided that the collimator assembly has a movable lamella system with lamellae adjustable in one or two spatial directions, through which the width and/or the length of one, several or all secondary openings are adjustable. This has the advantage that the width and/or length of secondary openings can be adjusted relatively quickly, and the mechanism can be made adjustable with little construction effort.

According to one advantageous embodiment of the invention it is provided that the movable lamella system has at least two individual lamellae arranged one behind the other in the direction of radiation of the X-rays, each having several radiolucent openings, and which are shiftable relative to one another. This allows a simple and reliable construction of the lamella system. The radiolucent openings, which can be designed like the secondary openings mentioned above, can, e.g., be slot-shaped.

According to one advantageous embodiment of the invention it is provided that at least the part of the collimator assembly, which has the secondary openings is bent about a spatial axis, in particular in a constant radius. In this way, the effectiveness of the secondary openings can be optimized.

According to one advantageous embodiment of the invention it is provided that the apparatus is arranged to carry out a method of the type described above. For example, the apparatus may have an electronic control unit which is arranged by means of programming to carry out the steps of the method according to the invention, e.g., to record the first and second parts of the projection images and to determine the X-ray image data set therefrom. The control unit can also be constructed to control the collimator assembly.

The invention addresses an advantageous possibility of compensating for the lost marginal region information in order to achieve high image quality with realistic Hounsfield values at a low X-ray dose. The invention primarily pursues the goal of an application in the field of therapy in which the volume of interest is known in advance. However, the invention can also be used for diagnostic applications.

A special feature of the invention is the ability to acquire partial information of the marginal region through a clever construction of individual or all collimator apertures. Here, the collimator apertures can be constructed in such a way that pockets ("slits", e.g., the previously mentioned openings) of a defined geometry are inserted in defined positions within the collimator. These pockets can, for example, be square, rectangular, circular or any other conceivable geometry. The pockets can be designed as complete material recesses or can be ensured by material thinning that allows photon detection above the electronic noise of the detector. It is also conceivable, for example, to design the radiolucent regions using inserts made of less X-ray-attenuating materials in order to continue to ensure a high mechanical load-bearing capacity. The image reconstruction process takes into account this information acquired section by section, which contributes to an improvement in image quality.

The exemplary technical construction of this system provides, among others, the following components:

- Lamellae of a highly attenuating, preferably metallic material (e.g., lead or tungsten) for collimation (adjustment of the beam path) in the z-direction
- Lamellae of a highly attenuating, preferably metallic material (e.g., lead or tungsten) for collimation (adjustment of the beam path) in the x-direction.
- The lamella system movable in the z-direction is preferably fully formed and bent around the z-axis but can also be designed slotted or planar.
- The lamella system movable in the z-direction can also be slotted in a defined manner and preferably bent around the z-axis. Wherein the slits preferably run parallel to the x-axis but can also be parallel to the z-axis or have other free spatial courses in the lamella plane.
- The lamella system movable in the x-direction is preferably slotted in a defined manner and preferably bent around the z-axis. Wherein the slits preferably run parallel to the z-axis but can also be parallel to the x-axis or have other free spatial courses in the lamella plane.
- The lamella system consists of a mechanism that makes it possible to change the size of the radiolucent regions of the lamella system via relative movements of two lamella components, right up to complete closure.

The advantage of the adaptive lamella system is that the projections required for imaging can be skillfully adjusted within a rotation or partial rotation of the CT or C-arm system so that data sets for calculating a CT data set with a required minimum image quality can be generated at a minimal dose.

For example, the lamella system can consist of two individual lamellae located one above the other, which have radiolucent pockets. These lamellae are positionable relative to each other. One aim of the construction of the lamellae is to ensure a free VOI area and to allow variable radiolucent zones to be freely adjustable in the marginal regions.

Another variant is the adjustability of the individual radiolucent pockets by means of decoupled sliding mechanisms, which for example can be driven individually by electric motors.

In a further advantageous embodiment, the lamella system is bent with a constant radius around the z-axis, whereby the edges of the pockets run parallel to the X-ray beam at all times and thus ensure a homogeneous attenuation. The radius is correspondingly individual for each lamella in a lamella system consisting of two individual lamellae lying on top of each other.

It is also conceivable to achieve a lamella system for the generation of volume areas of different geometric shapes, e.g., circular as in classic aperture systems in photography. The aim here is also to incorporate adaptive pockets into the lamella regions, which create defined radiolucent regions.

The invention is explained in more detail by means of embodiments using drawings.

It shows

Figure 1:
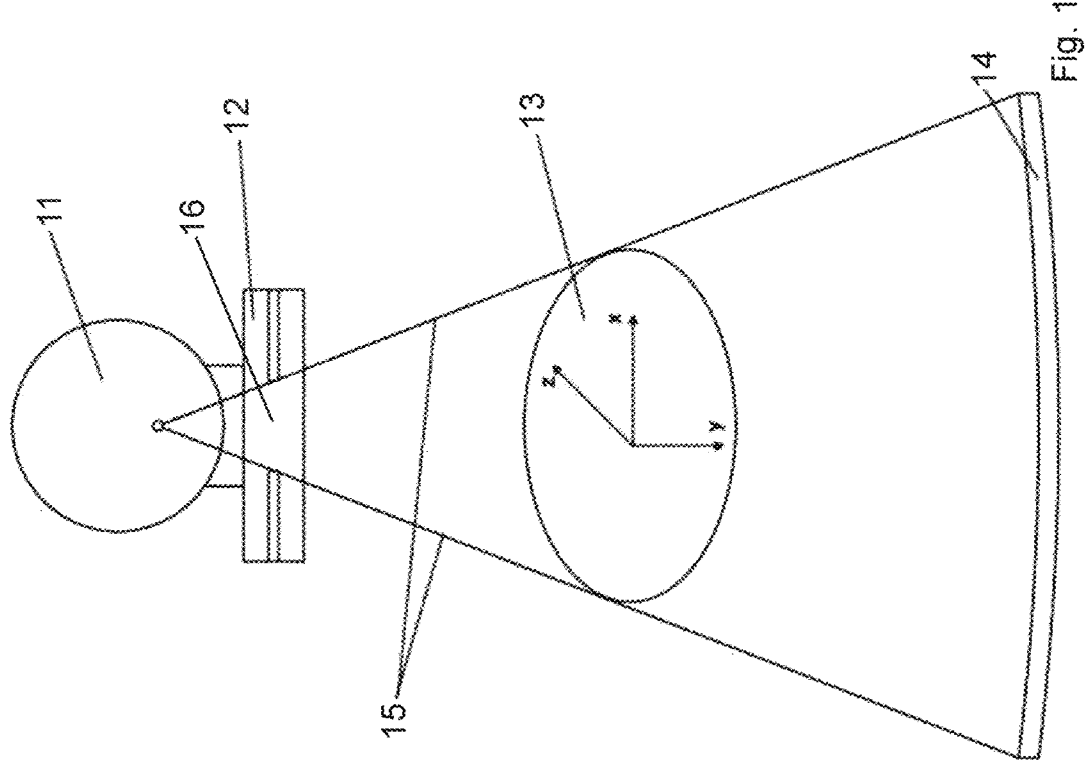
Figure 3:
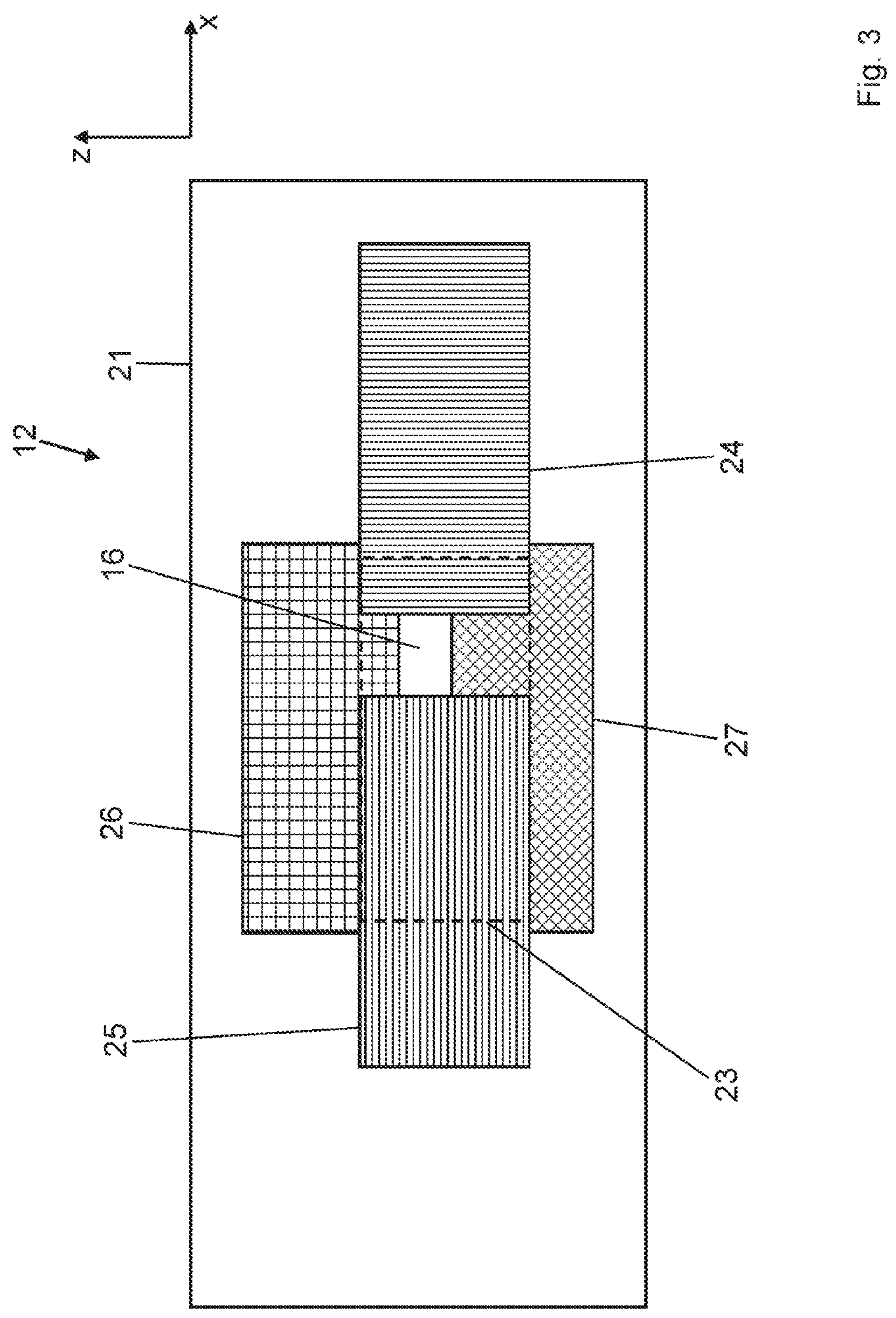
Figure 4:
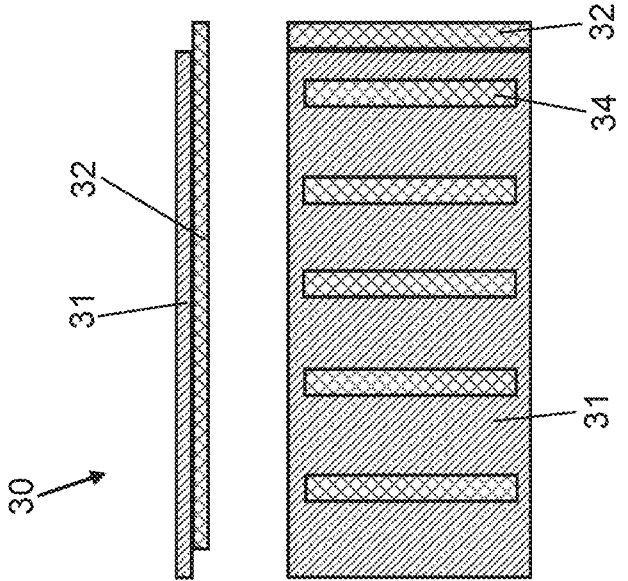
Figure 4:
Figure 4:
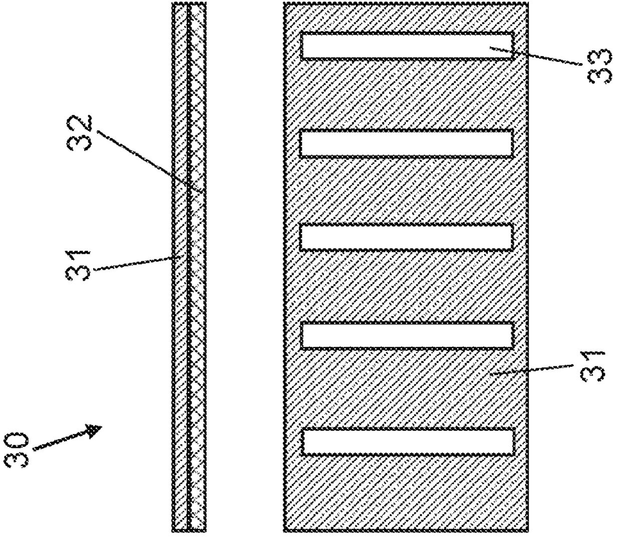

FIG. 1 the structure of an apparatus according to the invention in a viewing direction along the z-axis, FIG. 2 the structure of an apparatus according to the invention in a viewing direction along the x-axis, FIG. 3 a collimator assembly in plan view, FIG. 4 a movable lamella system in a first position, FIG. 5 the movable lamella system of FIG. 4 in a second position.

A coordinate system is assumed in which the beam direction of the X-rays runs in the y-direction. Accordingly, the collimator assembly extends in its planar dimension in the x-z plane or, in the case of a curved construction, slightly curved in relation to the x-z plane.

FIGS. 1 and 2 show an exemplary structure of an apparatus for determining an X-ray image data set of a target area 17 of an examination object 13. The apparatus has an X-ray device 11, e.g., an X-ray tube, by which X-rays are emitted onto the examination object 13 via a collimator assembly 12 and an X-ray detector 14 arranged behind the examination object 13 in the direction of radiation. The collimator assembly 12 has a main radiation opening 16, which can be adjusted with regard to its position and size, possibly also with regard to the radiolucency, by means of movable lamella systems of the collimator assembly 12.

It can be seen that the X-rays extend in a collimated beam path 15 through the target area 17 of the examination object 13 to the X-ray detector 14. The exposed regions are evaluated at the X-ray detector 14, e.g., by a matrix arrangement of X-ray-sensitive detector elements, from whose signals respective projection images can be formed. The apparatus also has a control unit, which is not shown in the Figures. The control unit is used to control the collimator assembly 12, to read out the data from the X-ray detector 14 and to determine the X-ray image data set from the projection images obtained by the X-ray detector 14.

FIG. 3 shows a schematic sketch of the collimator assembly 12. The collimator assembly 12 has a housing 21, in which four shiftable lamellae systems 24, 25, 26, 27 are arranged. The lamella systems 24, 25 are shiftable, for example, along the x-axis, the lamella systems 26, 27 along the z-axis. The lamella systems 24, 25 can be shifted to the left and right, thus towards or away from each other. The lamella systems 26, 27 can be moved upwards and downwards, thus towards or away from each other. The lamella systems 24, 25, 26, 27 can define a certain radiolucent area, which forms the main radiation opening 16, depending on the setting. FIG. 3 shows with the dashed line an example of the maximum possible opening range 23 of the lamella systems, e.g., the maximum size of the main radiation opening 16. The lamella systems can, for example, be controlled automatically, e.g., by means of a motor drive.

In order to form secondary radiation openings in the marginal regions of the target area 17, i.e., outside the main radiation opening 16, the lamella systems 24, 25, 26, 27 can have an additional function compared to simple shiftable apertures, which is explained with reference to FIGS. 4 and 5.

FIGS. 4 and 5 show by way of example on the basis of a lamella system 30, which can be used to realize one or more of the lamella systems 24, 25, 26, 27, an advantageous structure with an upper lamella 31 in the direction of radiation and a lower lamella 32 in the direction of radiation. FIGS. 4 and 5 show the lamella system in a side view above and in a plan view below.

The upper lamella 31 and the lower lamella 32 each have exactly or at least substantially congruent radiation openings 33, e.g., in the form of slit-shaped openings 33. If the upper lamella 31 and the lower lamella 32 are arranged exactly aligned above one another, as shown in FIG. 4, their radiation openings 33 are also aligned with one another, so that a plurality of secondary radiation openings are thereby formed in the marginal regions around the main radiation opening 16. If the upper lamella 31 and the lower lamella 32 are shifted relative to each other, as shown in FIG. 5, the secondary radiation openings formed by the aligned radiation openings 33 are closed, since the radiation openings of the upper lamella 31 are covered by the lower lamella 32, and the radiation openings of the lower lamella 32 are covered by the upper lamella 31. This is illustrated in FIG. 5 by the closed openings 34 of the upper lamella 31.

The invention claimed is:

1. Method for determining an X-ray image data set of a target area of an examination object, the method comprising the steps of:

taking projection images showing the target area using an X-ray detector, wherein a first part of the projection images is taken collimated onto the target area by irradiating the target area with X-ray radiation using an X-ray device through at least one main radiation opening of a collimator assembly and wherein a second part of the projection images is taken in order to reduce truncation artefacts in the X-ray image data set by irradiating marginal regions of the target area with X-ray radiation through one or several secondary radiation openings, which are arranged in one or several collimator apertures of the collimator assembly, and which surround the main radiation opening or are adjacent to it; and reconstructing the X-ray image data set from the projection images, wherein the X-ray image data set is reconstructed from the first part of the projection images with the aid of the second part of the projection images.

2. Method according to claim 1, wherein the step of taking projection images comprises varying the size, position and/or radiation transmittance of one, several or all secondary radiation openings during an X-ray examination of the target area.

3. Method according to claim 2, wherein the variation of the size, position and/or radiation transmittance of one, several or all secondary radiation openings is carried out adaptively in dependence of the respective quality of the present X-ray images.

4. Method according to claim 1, wherein the method further comprises automatically detecting irradiated and non-irradiated regions of the X-ray detector and automatically considering detected irradiated and non-irradiated regions of the X-ray detector.

5. Method according to claim 1, wherein the method further comprises automatically detecting scattered radiation of the emitted X-ray radiation in regions of the X-ray detector, which are not directly irradiated, and automatically considering detected scattered radiation.

6. Apparatus for determining an X-ray image data set of a target area of an examination object, having an X-ray detector for taking projection images showing the target area and a reconstruction means for reconstructing the X-ray image data set from the projection images, further having an X-ray device and a collimator assembly having at least one main radiation opening for taking a first part of the projection images, which are taken collimated onto the target area by the target area being irradiated with X-ray radiation by means of an X-ray device, characterized in that the collimator assembly has one or several secondary radiation openings, which are arranged in one or several collimator apertures and which surround the main radiation opening or are adjacent to it, wherein a second part of the projection images is taken by irradiating marginal regions of the target area with X-ray radiation through one or several secondary radiation openings, wherein the reconstruction means is arranged to determine the X-ray image data set from the first part of the projection images with the aid of the second part of the projection images to reduce truncation artefacts in the X-ray image data set.

7. Apparatus according to claim 6, characterized in that the collimator assembly is arranged to adjust the width and/or the length of one, several or all secondary radiation openings.

8. Apparatus according to claim 7, characterized in that the collimator assembly has a movable lamella system with lamellae adjustable in one or two spatial directions, by which the width and/or the length of one, several or all secondary openings are adjustable.

9. Apparatus according to claim 8, characterized in that the movable lamella system has at least two individual lamellae arranged one behind the other in the direction of radiation of the X-rays, which each have several radiation transmitting openings, and which are shiftable relative to one another.

10. Apparatus according to claim 6, characterized in that at least the part of the collimator assembly, which has the secondary openings is bent about a spatial axis, in particular in a constant radius.

11. Apparatus for determining an X-ray image data set of a target area of an examination object, having an X-ray detector for taking projection images showing the target area and a reconstruction means for reconstructing the X-ray image data set from the projection images, further having an X-ray device and a collimator assembly having at least one main radiation opening for taking a first part of the projection images, which are taken collimated onto the target area by the target area being irradiated with X-ray radiation by means of an X-ray device, characterized in that the collimator assembly has one or several secondary radiation openings, which surround the main radiation opening or are adjacent to it, wherein a second part of the projection images is taken by irradiating marginal regions of the target area with X-ray radiation through one or several secondary radiation openings, wherein the reconstruction means is arranged to determine the X-ray image data set from the first part of the projection images with the aid of the second part of the projection images to reduce truncation artefacts in the X-ray image data set, characterized in that the apparatus is adjusted to carry out a method according to claim 1.

* * * * *